United States Patent
Prakash et al.

(10) Patent No.: US 6,281,380 B1
(45) Date of Patent: Aug. 28, 2001

(54) SYNTHESIS OF N-(N-(3,3-DIMETHYLBUTYL)-L-α-ASPARTYL)L-PHENYLALANINE1-METHYL ESTER BY REDUCTIVE ALKYLATION AND CRYSTALLIZATION/ISOLATION IN AQUEOUS METHANOL

(75) Inventors: Indra Prakash, Hoffman Estates; Mike G. Scaros, Arlington Heights; Kurt L. Wachholder, Elgin, all of IL (US)

(73) Assignee: The Nutra Sweet Company, Chicago, IL (US)

( * ) Notice: Subject to any disclaimer, the term of this patent is extended or adjusted under 35 U.S.C. 154(b) by 0 days.

(21) Appl. No.: 09/572,843

(22) Filed: May 18, 2000

(51) Int. Cl.⁷ .................................................. C07C 229/00
(52) U.S. Cl. ............................................. 560/40; 560/41
(58) Field of Search ......................................... 560/40, 41

(56) References Cited

U.S. PATENT DOCUMENTS 5,480,668 * 1/1996 Nofre et al. .
5,502,238 * 3/1996 Rijkers et al. .
5,728,862 * 3/1998 Prakash .

OTHER PUBLICATIONS

Derwent abstract (1999–302719) of WO 9920648 A1. Amino et al. Purifying N–(N–(3,3–dimethylbutyl)–L–aspartyl–L–phenylalanine methyl ester. Apr. 1999.*
CAPLUS abstract (1999:736740) of WO 9958554 A. Kishishita et al. Novel aspartame derivative crystal process for producing the same. Nov. 1999.*
CAPLUS abstract (2000:31475) of WO 200026234 A1. Kawahara et al. Crystallization processes of stable crystals of aspartame derivatives. May 11, 2000.*
Derwent abstract (1999–39508) of JP 11169133 A. Kishishita et al. Preparation of aspartame and aspartame derivative, Jun. 1999.*

* cited by examiner

Primary Examiner—Paul J. Killos
Assistant Examiner—Mahreen Chaudhry

(57) ABSTRACT

N-[N-(3,3-dimethylbutyl)-L-α-aspartyl]-L-phenylalanine 1-methyl ester is produced by reductive alkylation and crystallization/isolation in methanol and water. The production method is efficient and low cost, as compared with conventional N-[N-(3,3-dimethylbutyl)-L-α-aspartyl]-L-phenylalanine 1-methyl ester synthesis and results in high purity N-[N-(3,3-dimethylbutyl)-L-α-aspartyl]-L-phenylalanine 1-methyl ester.

15 Claims, No Drawings

SYNTHESIS OF N-(N-(3,3-DIMETHYLBUTYL)-L-α-ASPARTYL)L-PHENYLALANINE1-METHYL ESTER BY REDUCTIVE ALKYLATION AND CRYSTALLIZATION/ ISOLATION IN AQUEOUS METHANOL

BACKGROUND OF THE INVENTION

1. Field of the Invention

This invention relates to the synthesis of N-[N-(3,3-dimethylbutyl)-L-α-aspartyl]-L-phenylalanine 1-methyl ester (neotame) by reductive alkylation and crystallization/isolation in methanol and water. This method of producing neotame results in high purity and is more simple and more economical than the typical preparation of neotame.

2. Related Background Art

N-[N-(3,3-dimethylbutyl)-L-α-aspartyl]-L-phenylalanine 1-methyl ester (neotame) is a high potency dipeptide sweetener (about 8000× sweeter than sucrose) that has the formula

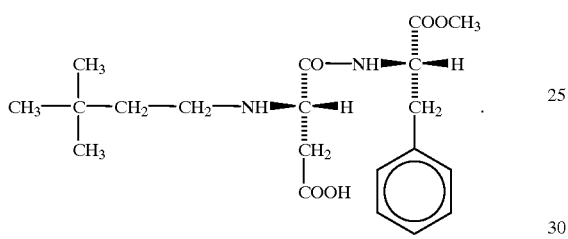

The chemical synthesis of neotame is disclosed in U.S. Pat. Nos. 5,480,668, 5,510,508, 5,728,862 and WO 00/15656, the disclosure of each of which is incorporated by reference herein.

U.S. Pat. No. 5,480,668 describes the formation of neotame in methanol, followed by methanol removal, formation of an aqueous hydrochloric acid solution of the neotame, filtration, drying and recrystallization from an ethanol/water mixture.

U.S. Pat. No. 5,510,508 describes the formation of neotame in aqueous acetic acid and methanol, followed by methanol removal, filtration, drying and washing.

U.S. Pat. No. 5,728,862 describes the formation of neotame in methanol, followed by filtration, washing, methanol reduction, addition of water, methanol distillation, filtration, washing and drying.

WO 00/15656 describes the formation of neotame using Z-aspartame (N-benzyloxycarbonyl-L-α-aspartyl-L-phenylalanine-1-methyl ester) in a methanolic solvent, followed by partial evaporation of the organic part of the solvent, optional addition of water before and/or during and/or after the partial evaporation of the organic part of the solvent, separation of the neotame formed and drying.

In addition to being complicated by various methanol removal and/or distillation steps, these chemical processes may produce several troublesome impurities, including N,N-di(3,3-dimethylbutyl)-L-aspartyl-L-phenylalanine methyl ester (dialkylated aspartame), α-methyl hydrogen-3-( 3,3-dimethylbutyl)-2-L-(2,2-dimethylpropyl)-5-oxo-α-L-(phenylmethyl)-1,4(L)-imidazolidine diacetate (dialkylated imidazolidinone), N-[N-(3,3-dimethylbutyl)-L-α-aspartyl]-L-phenylalanine (demethylated α- or β-neotame) and methyl ester of N-[N-(3,3-dimethylbutyl)-L-α-aspartyl]-L-phenylalanine 1-methyl ester (methylated α- or β-neotame). These impurities are represented respectively by the structural formulae:

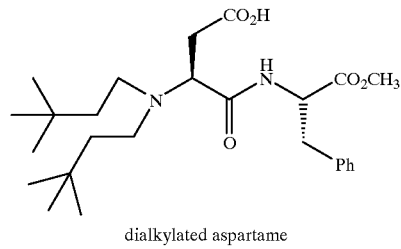

dialkylated aspartame

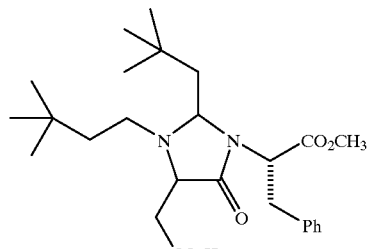

dialkylated imidazolidinone

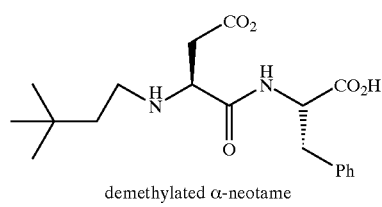

demethylated α-neotame

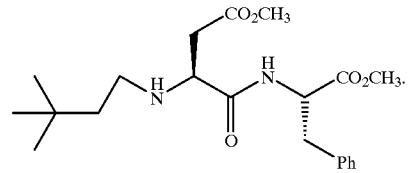

methylated α-neotame

Since neotame is mainly employed in foods for human consumption, it is extremely important that neotame exist in a highly purified state.

U.S. Pat. No. 5,728,862 outlines a purification method by which neotame is precipitated out of an aqueous/organic solvent solution, wherein the aqueous/organic solvent solution has an amount of organic solvent of about 17% to about 30% by weight.

Copending U.S. patent application Ser. No. 09/448,671, filed on Nov. 24, 1999, relates to methods of purifying neotame by crystallization in a variety of organic solvent/aqueous organic solvent mixtures. Each of these methods which uses an organic solvent and water mixture contemplates a solvent distillation step.

Thus, it is clear that there is a need to economically and efficiently produce pure N-[N-(3,3-dimethylbutyl)-L-α-aspartyl]-L-phenylalanine 1-methyl ester.

SUMMARY OF THE INVENTION

The present invention relates to the efficient, low cost and high purity synthesis of N-[N-(3,3-dimethylbutyl)-L-α-aspartyl]-L-phenylalanine 1-methyl ester. According to the present inventive method, neotame is synthesized by preparing a mixture of aspartame and a catalyst in a solvent consisting of water and methanol; adding 3,3-dimethylbutyraldehyde to the mixture in the presence of hydrogen to produce N-[N-(3,3-dimethylbutyl)-L-α-aspartyl]-L-phenylalanine 1-methyl ester; removing the catalyst; adding water to the mixture to reach a desired crystallization solvent concentration; holding the mixture for a time and at a temperature sufficient to hydrolyze dialkylated imidazolidinone; and crystallizing N-[N-(3,3-dimethylbutyl)-L-α-aspartyl]-L-phenylalanine 1-methyl ester.

In certain preferred embodiments of the present invention, crystallized N-[N-(3,3-dimethylbutyl)-L-α-aspartyl]-L-phenylalanine 1-methyl ester is separated from the mixture.

In a certain embodiment of the present invention, the mixture may be seeded prior to crystallization.

DETAILED DESCRIPTION

The present invention relates to the optimization of the synthesis of N-[N-(3,3-dimethylbutyl)-L-α-aspartyl]-L-phenylalanine 1-methyl ester (neotame) by reductive alkylation in a water/methanol solvent in order to produce substantially pure neotame.

According to the present invention, N-[N-(3,3-dimethylbutyl)-L-α-aspartyl]-L-phenylalanine 1-methyl ester is synthesized by preparing a mixture of aspartame and a catalyst in a solvent consisting of water and methanol; adding 3,3-dimethylbutyraldehyde to the mixture in the presence of hydrogen to produce N-[N-(3,3-dimethylbutyl)-L-α-aspartyl]-L-phenylalanine 1-methyl ester; removing the catalyst; adding water to the mixture to reach a desired crystallization solvent concentration; holding the mixture for a time and at a temperature sufficient to hydrolyze dialkylated imidazolidinone; and crystallizing N-[N-(3,3-dimethylbutyl)-L-α-aspartyl]-L-phenylalanine 1-methyl ester.

According to the first step of the present inventive method, a mixture of aspartame and a catalyst is prepared in a solvent consisting of water and methanol. The ratio of water to methanol in the solvent is from about 5:95 to about 70:30, and preferably from about 30:70 to about 50:50.

The concentration of aspartame in the water and methanol mixture is from about 5% to about 25%, and preferably about 17%. The aspartame used in the present inventive process can be wet with water or dry. Aspartame can also be used in situ from any N-protected aspartame derivative prepared by known methods.

The catalyst suitable for use in the present invention may be selected from catalysts based on palladium or platinum including, without limitation, platinum on activated carbon, palladium on activated carbon, platinum black or palladium black. Other catalysts include, without limitation, nickel on silica, nickel on alumina, Raney nickel, ruthenium black, ruthenium on carbon, palladium hydroxide on carbon, palladium oxide, platinum oxide, rhodium black, rhodium on carbon and rhodium on alumina. The catalysts based on palladium or platinum are preferred.

The catalyst is present in an amount effective to produce neotame in an acceptable yield. Generally, the weight ratio of catalyst (on a dry basis) to aspartame is about 0.01:1 to about 0.25:1, preferably about 0.10:1. It is important to note that about a 10% catalyst loading is required to minimize the undesirable yield of dialkylated aspartame.

According to the second and third steps of the present invention, 3,3-dimethylbutyraldehyde is added to the mixture and reacted with aspartame in the presence of the catalyst and in the presence of hydrogen for a time and at a temperature sufficient to produce neotame. 3,3-Dimethylbutyraldehyde can be added slowly or all at once to the reaction mixture. When the aldehyde is gradually added, typically it is added over the course of about 2 to 8 hours, preferably from about 4 to 6 hours. It is important to note that the reactants, i.e., aspartame, catalyst, aldehyde, can be added in any order.

Aspartame (L-α-aspartyl-L-phenylalanine 1-methyl ester) and 3,3-dimethylbutyraldehyde are readily available starting materials, which are typically combined in a substantially equivalent molar ratio, i.e., about 1:0.95 to 1:1. Excess molar amounts of aspartame are not preferred due to waste and cost. Higher molar amounts of the aldehyde are likely to lead to the generation of impurities. Further, the 3,3-dimethylbutyraldehyde used in the present process should be highly pure. Small impurities in the 3,3-dimethylbutyraldehyde may produce odor. Higher molar ratios of aldehyde may cause the entrapment of the aldehyde during the crystallization of neotame and produce odor; alternatively, excess aldehyde may be oxidized to the corresponding t-butyl acetic acid which also produces odor. The odor can be removed by washing the final product with organic solvents (such as heptane, ethyl acetate, t-butylmethyl ether, hexane, etc.) or by extruding the final product. The excess aldehyde may also react with neotame to give dialkylated imidazolidinone. This may also be crystallized along with neotame and will hydrolyze to give neotame and aldehyde.

The aldehyde and the aspartame are reacted for a time and at a temperature sufficient to produce neotame. Generally, the time ranges from about 1 to about 24 hours, preferably from about 2 to about 4 hours after the addition of the aldehyde is complete. If the 3,3-dimethylbutyraldehyde is added to the reaction mixture all at once, then the time sufficient to produce neotame preferably ranges from about 6 to about 24 hours. Generally, the temperature sufficient to produce neotame according to the present invention ranges from about 20° C. to about 60° C., preferably from about 22° C. to about 40° C.

The reaction of the present invention is carried out in the presence of hydrogen. Generally, the pressure of the hydrogen ranges from about 5 psi to about 100 psi, preferably from about 30 psi to about 40 psi.

In the next step of the present inventive method, the catalyst is removed from the mixture. The catalyst may be separated by a variety of solid-liquid separation techniques that include, without limitation, the use of sparkler, crossflow, nutsche, basket, belt, disc, drum, cartridge, candle, leaf and bag filters. Furthermore, catalyst separation performance may be enhanced through the use of gravity, pressure, vacuum and/or centrifugal force. Additionally, the catalyst separation rate and removal efficiency may be enhanced through the use of any number of various filter media that include, without limitation, woven cloth fabrics, woven metal fabrics, porous metal substrates and synthetic or naturally occurring membranes. The separation device and media can be permanent, replaceable or disposable. The catalyst solid alone may be separated, or separation may be assisted by the use of porous cellulosic fiber or diatomaceous silica type filter aids, which are used as a media precoat and/or directly with a catalyst slurry. The separation device can be operated in an automated or manual mode for solid media washing, solid discharging and/or solid and media back flushing. The catalyst can be washed and discharged from the filter media using gas, liquid or mechanical means. The catalyst alone or catalyst with filter aid can be partially or totally recycled for used in subsequent hydrogenation reactions.

In the fourth step of the present invention, water is added to the mixture to reach a desired solvent concentration. The ratio of water to methanol in the crystallization solvent is from about 85:15 to about 65:35, and preferably from about 75:25 to about 70:30.

In the next step of the present process, the mixture is held for a time and at a temperature sufficient to hydrolyze dialkylated imidazolidinone to α-neotame and 3,3-dimethylbutyraldehyde. The reaction mixture is generally held for about 0.5–24 hours at a temperature of about 20–50° C. In a preferred embodiment of the present invention, the reaction mixture is held for about 2–4 hours.

In the final step of the present inventive process, neotame is crystallized. Typically this is accomplished by cooling the mixture to about 0–250° C., preferably to about 5–10° C., over the course of about 0.5–2 hours, preferably about 1–2 hours.

Seeding prior to or during crystallization can initiate a controlled crystal growth rate according to the present invention. Hence, the reaction mixture may optionally be seeded in an amount from 0.0001%–10%, by weight of the N-[N-(3,3-dimethylbutyl)-L-a-aspartyl]-L-phenylalanine 1-methyl ester in the solution, preferably from 0.1% to 1% and most preferably from 0.1% to 0.5%. Seeding is typically performed at 25–35° C. and preferably at 28–30° C.

The reaction mixture or the solution containing neotame may be unstirred or stirred during the crystallization processes of the present invention.

The crystallized neotame may be separated from the solvent solution by a variety of solid-liquid separation techniques that utilize centrifugal force, that include, without limitation, vertical and horizontal perforated basket centrifuge, solid bowl centrifuge, decanter centrifuge, peeler type centrifuge, pusher type centrifuge, Heinkel type centrifuge, disc stack centrifuge and cyclone separation. Additionally, separation may be enhanced by any of pressure, vacuum, and gravity filtration methods, that include, without limitation, the use of belt, drum, nutsche type, leaf, plate, Rosenmund type, sparkler type, and bag filters and filter press. Operation of the neotame solid-liquid separation device may be continuous, semi-continuous or in batch mode. The neotame solid may also be washed on the separation device using various liquid solvents, including, without limitation, water, methanol and mixtures thereof. The neotame solid can also be partially and totally dried on the separation device using any number of gases, including, without limitation, nitrogen and air, to evaporate residual liquid solvent. The neotame solid may be automatically or manually removed from the separation device using liquids, gases or mechanical means by either dissolving the solid or maintaining the solid form.

The product isolated from this method is the monohydrate, which may be dried to produce an anhydrous form.

The crystallized and isolated neotame solid may be further purified by a variety of drying methods. Such methods are known to those skilled in the art and include, but are not limited to, the use of a rotary vacuum dryer, fluid bed dryer, rotary tunnel dryer, plate dryer, tray dryer, Nauta type dryer, spray dryer, flash dryer, micron dryer, pan dryer, high and low speed paddle dryer and microwave dryer.

The above-described process of the present invention achieves a number of advantages as compared to conventional neotame synthetic routes. In particular, methanol removal or distillation steps are eliminated. On a manufacturing scale, this results in at least a 2–3 days processing time savings, as well as a significant cost savings. Dialkylated imidazolidinone hydrolysis time is also reduced to only two hours according to the present invention. Further, additional reduction in cost is achieved due to the higher aspartame concentration employed in the present invention.

Additionally, as compared to methods using 100% methanol, safety concerns are lessened and the amount of α-methyl hydrogen-3-(3,3-dimethylbutyl)-2-L-(2,2-dimethylpropyl)-5-oxo-α-L-(phenylmethyl)-1,4(L)-imidazolidine diacetate (dialkylated imidazolidinone) is significantly lower.

The Examples which follow are intended as an illustration of certain preferred embodiments of the invention, and no limitation of the invention is implied.

EXAMPLE 1

One hundred grams aspartame was charged to a 1.0 L RC 1 glass vessel having an agitator operating at 100 rpm. Twenty-six grams 5% Pd/C catalyst (10% loading on dry basis; 61.45% wet) was then charged to the vessel. One hundred grams water and 375 g methanol were also charged to the vessel. The vessel was then purged with nitrogen (4×). While under 10 psig nitrogen, the vessel was heated to 40° C. Then the vessel was purged with hydrogen (4×) and charged to 40 psig hydrogen. The agitator was set to 800 rpm. Then 33.2 g 3,3-dimethylbutyraldehyde was pumped into the vessel over 5 hours. The 3,3-dimethylbutyraldehyde container, the pump and the lines were rinsed with approximately 5 ml methanol (3×). The mixture was stirred for an additional 2 hours at 40 psig and 40° C.

At the completion of the reductive alkylation, the vessel was vented and purged with nitrogen (4×). The catalyst was removed by filtration through a layer of powdered cellulose using a Buchner glass filter. The vessel was rinsed with 335 ml deionized water; this water was used to wash the catalyst and combined with the filtrate.

An HPLC (high pressure liquid chromatography) analysis of the crude mixture thus obtained indicates the following: 91.0% neotame, 4.0% aspartame, 1.23% dialkylated aspartame, 0.26% dialkylated imidazolidinone and 0.25% methylated neotame. The filtrate containing this crude mixture was then placed in a jacketed flask, heated to 40° C. and held for 2 hours to hydrolyze the dialkylated imidazolidinone. The solution was then cooled to 28° C. and seeded with 0.17 g neotame. After seeding, the crystallizer was cooled to 5° C. over 1.5 hour. The neotame slurry was held at 5° C. for 1 hour. Then the neotame was filtered, and the wet cake was washed with 70 ml cold deionized water. The isolated neotame was dried at 40° C. under vacuum with nitrogen purge for 48 hours.

Neotame was obtained in 70.74% yield. An HPLC analysis of the final product indicated the following: >98% neotame, 0.0% aspartame, 0.03% dialkylated aspartame, 0.00% dialkylated imidazolidinone and 0.04% methylated neotame.

EXAMPLE 2

One hundred grams aspartame was charged to a 1 L stirred vessel. Twenty-six grams of 5% Pd/C catalyst (61.45% water) was charged to the reactor. Two hundred fifty grams water followed by 375 g methanol were added to the reactor. The vessel was purged with nitrogen (4×). While under nitrogen pressure (10 psig), the contents of the vessel were heated to 40° C. Then the vessel was purged with hydrogen (4×) and charged to 40 psig with hydrogen. The agitator was set to 800 rpm. Then 33.2 g of 3,3-dimethylbutyraldehyde was pumped into the vessel over 5 hours. The pump and transfer lines were rinsed with 3 ml methanol (3×) to ensure complete and accurate charging. The mixture was stirred for an additional two hours at 40 psig and 40° C.

After completion of the reductive alkylation, the vessel was vented and purged with nitrogen (4×). The catalyst was removed by filtration through powdered cellulose on a Buchner funnel. The vessel was rinsed with 185 g deionized water. This rinse was also used to wash the catalyst and combined with the filtrate. After addition of the water, the solution is heated to 40° C. for two hours to hydrolyze the dialkylated imidazolidinone. The product was isolated as described in Example 1.

Neotame was obtained in 70% yield. An HPLC analysis of the final product indicated the following: >98% neotame, <0.05% dialkylated aspartame and <0.05% methylated neotame.

Other variations and modifications of this invention will be obvious to those skilled in this art. This invention is not to be limited except as set forth in the following claims.

What is claimed is:

1. A process of synthesizing N-[-(3,3-dimethylbutyl)-L-α-aspartyl]-L-phenylalanine 1-methyl ester comprising the steps of:
   (a) preparing a mixture of L-α-aspartyl-L-phenylalanine 1-methyl ester and a catalyst in a solvent consisting of an amount of water and methanol at a ratio of 5:95 to 60:40;
   (b) adding 3,3-dimethylbutyraldehyde gradually to the mixture wherein the ratio of L-α-aspartyl-L-phenylalanine 1-methyl ester to 3,3-dimethylbutyraldehyde is from 1:0.95 to about 1:1;
   (c) reacting the L-α-aspartyl-L-phenylalanine 1-methyl ester and the 3,3-dimethylbutyraldehyde in the presence of the catalyst and in the presence of hydrogen at about 5 psi to about 100 psi and at a temperature of about 20° C. to about 60° C. and for a time of about 1 hour to about 24 hours;
   (d) removing the catalyst;
   (e) adding water to the mixture, wherein the ratio of water to methanol is from 85:15 to 65:35;
   (f) holding the mixture for a time of 0.5 to 24 hours at between 20° C. to 50° C.;
   (g) crystallizing N-[N-(3,3-dimethylbutyl)-L-α-aspartyl]-L-phenylalanine 1-methyl ester, wherein said crystallization is accomplished by cooling the mixture to a temperature of from about 0° C. to 25° C. over a period of 0.5 to 2 hours; and
   (h) isolating the crystallized N-[N-(3,3dimethylbutyl)-L-α-aspartyl]-L-phenylalanine 1-methyl ester.

2. The process according to claim 1, additionally comprising the step of seeding with an amount of N-[N-(3,3-dimethylbutyl)-L-α-aspartyl]-L-phenylalanine 1-methyl ester during step (f) or step (g).

3. The process according to claim 1, wherein the solvent consists of an amount of water and methanol at a ratio of 30:70 to 50:50.

4. The process according to claim 1, wherein the catalyst is selected from the group consisting of platinum on activated carbon, palladium on activated carbon, platinum black, palladium black, nickel on silica, nickel on alumina, Raney nickel, ruthenium black, ruthenium on carbon, palladium hydroxide on carbon, palladium oxide, rhodium black, rhodium on carbon and rhodium on alumina.

5. The process according to claim 4, wherein the catalyst is a palladium or platinum catalyst.

6. The process according to claim 1, wherein said 3,3-dimethylbutyraldehyde in step (b) is added slowly over a period of 2 to 6 hours.

7. The process according to claim 1, wherein the temperature of step (c) is from about 22° C. to about 40° C.

8. The process according to claim 1, wherein the time of step (c) is from about 2 hours to about 4 hours.

9. The process according to claim 1, wherein the pressure of the hydrogen in step (c) is from about 30 psi to about 40 psi.

10. The process according to claim 1, wherein the ratio of water to methanol in step (e) is from about 75:25 to 70:30.

11. The process according to claim 1, wherein the time of holding of said mixture in step (f) is between about 2 to about 4 hours.

12. The process according to claim 2, wherein the amount of seed is from 0.0001% to 10% by weight of the N-[N-3,3-dimethylbutyl)-L-α-aspartyl]-L-phenylalanine methyl ester.

13. The process according to claim 12, wherein the amount of seed is from 0.01% to 1% by weight of the N-[N-(3,3-dimethylbutyl)-L-α-aspartyl]-L-phenylalanine methyl ester.

14. The process according to claim 1, wherein said crystallization of step (g) is accomplished by cooling the mixture to a temperature of from about 5° C. to 10° C. over a period of 1 to 2 hours.

15. The process according to claim 1, wherein said crystallization step (g) is stirred or unstirred.

* * * * *